United States Patent [19]

Wallsten

[11] Patent Number: 4,655,771

[45] Date of Patent: Apr. 7, 1987

[54] PROSTHESIS COMPRISING AN EXPANSIBLE OR CONTRACTILE TUBULAR BODY

[75] Inventor: Hans I. Wallsten, Denens, Switzerland

[73] Assignee: Shepherd Patents S.A., Delemont, Switzerland

[21] Appl. No.: 571,549

[22] PCT Filed: Apr. 11, 1983

[86] PCT No.: PCT/SE83/00131

§ 371 Date: Dec. 7, 1983

§ 102(e) Date: Dec. 7, 1983

[87] PCT Pub. No.: WO83/03752

PCT Pub. Date: Nov. 10, 1983

[30] Foreign Application Priority Data

Apr. 30, 1982 [SE] Sweden .................................. 8202739

[51] Int. Cl.⁴ ............................................... A61F 2/06
[52] U.S. Cl. ........................................... 623/1; 623/12; 623/66; 128/334 R; 128/335; 128/343; 604/281; 604/282
[58] Field of Search ............ 3/1.4; 128/334 R, 334 C, 128/335, 341, 343; 604/281, 282, 8

[56] References Cited

U.S. PATENT DOCUMENTS

| | | | |
|---|---|---|---|
| 3,509,883 | 5/1970 | Dibelius | 128/334 R |
| 3,822,238 | 7/1974 | Blair et al. | 3/1 X |
| 3,868,956 | 3/1975 | Alfidi et al. | 128/345 |
| 3,993,078 | 11/1976 | Bergentz et al. | 128/334 |
| 4,130,904 | 11/1978 | Whalen | 3/1.4 |
| 4,140,126 | 2/1979 | Choudhury | 604/8 X |
| 4,441,215 | 4/1984 | Kaster | 128/334 R X |

FOREIGN PATENT DOCUMENTS

| | | | |
|---|---|---|---|
| 8002461 | 12/1980 | Sweden | 3/1.4 |
| 1205743 | 9/1970 | United Kingdom | 128/343 |

Primary Examiner—Richard J. Apley
Assistant Examiner—Alan W. Cannon
Attorney, Agent, or Firm—Burns, Doane, Swecker & Mathis

[57] ABSTRACT

A prosthesis for transluminal implantation comprising a flexible tubular body which has a diameter that is variable by axial movement of the ends of the body relative to each other and which is composed of several individual rigid but flexible thread elements each of which extends in helix configuration with the center line of the body as a common axis, a number of elements having the same direction of winding but being axially displaced relative to each other crossing a number of elements also axially displaced relative to each other but having the opposite direction of winding; and method for transluminal implantation.

12 Claims, 14 Drawing Figures

PROSTHESIS COMPRISING AN EXPANSIBLE OR CONTRACTILE TUBULAR BODY

TECHNICAL FIELD

The present invention relates to a prosthesis which can be applied within or replace part of for example blood vessels of the body of a living animal or a living human or in some other difficultly accessible place. The prosthesis includes a flexible tubular body, the diameter of which can be decreased or increased. The invention is particularly useful for mechanical transluminal implantation by means of an expanded self-fixating prosthesis for blood vessels, respiratory tracts or the like. By means of the device of the present invention also the inner walls of damaged blood vessels or other organs may be lined with artificial tissue.

In surgical and other medicinal tecniques there is sometimes a need of inserting and expanding a device in for example blood vessel, urinary tracts or other difficultly accessible places which has for its function to support the vessel or tract which can be left in a position.

The device according to the present invention can be used also in many medicinal applications and, as examples, there may be mentioned utilization in different types of aneurism reflected by some form of vessel widening, or the opposite, stenosis, which involves contraction of blood vessels. Thus, more specifically, the invention can be used to support and keep open vessels of venous systems, to close pathological vessel failures, to bridge pathological vessel dilatations and ruptures in interior vessel walls or to stabilize bronchial tubes and bronchi. The device according to the present invention may also be designed to act as a filter for thrombosis, for example by application in Vena Cava Inferior to prevent the formation of lung emboliae. The invention is particularly suited to be used as a prosthesis, for example a graft, for application in blood vessels or other tubular organs within the body. It should, however, be observed that the invention is not limited to the applications mentioned which must be considered as solely exemplifying.

BACKGROUND ART

In U.S. Pat. No. 3,868,956 there is described a device which after insertion into for example blood vessel may be expanded. The active part of this device is based on the use of metal alloys having so-called "memory function", i.e. a material which when heated will recover its initial configuration. In this prior art the heating of the material is provided by electrical heating, the device being inserted at the location of interest. However, this known technique possesses the essential disadvantage that electrical resistance heating must take place in connection to surrounding sensitive tissue which may be damaged in the heating. It is true that it is stated in the patent specification (cf. col. 3, lines 42-48) that when inserting the device into a blood vessel the patient's blood functions as a cooling medium. However, also blood is a heat-sensitive material which when heated can be subjected to undesirable coagulation.

SUMMARY OF THE INVENTION

The present invention has for its purpose to provide a radially expansible and contractile prosthesis whereby the drawbacks of the known techniques are avoided.

The present invention is based on utilization of a prosthesis comprising a flexible tubular body the diameter of which can be changed by axial movement of the ends of the body relative to each other. In a preferred embodiment the body takes a radially expanded position by itself. When it is left in an unloaded condition free of external forces in radial direction. The body is composed of several individual rigid but flexible thread elements each of which extends in helix configuration with the center line of the body as a common axis. A number of elements have the same direction of winding but are displaced axially relative to each other. The said number of elements having the same direction of winding meet under crossing a number of thread elements also axially displaced to each other but having the opposite direction of winding.

To obtain the desired function the axially directed angle between crossing elements is suitably greater than about 60° and is preferably obtuse, i.e. more than about 90°. This state of the body refers to its state in radially unloaded condition.

It is preferred to arrange the crossing thread elements in such a manner as to form a sort of braided configuration which may be varied as desired and for example imitate some known type of weaving, for example according to the principle of a plain weave. The object of this is to impart to the tubular body the necessary stability. If the number of elements in the flexible tubular body is designated n it is preferred that n varies from about 10 and up, for example to about 50. The elements of the tubular body are preferably arranged symmetrically, i.e. the number of elements in each direction of a winding is (n/2). It should be observed that in this connection when referring to the number of elements in the tubular body reference is always had to elements intended to maintain the supporting function of the body. The number of elements n is selected in accordance with the diameter of the body, the diameter of the element, the material of the element or other factors. Quite generally, the greater the diameter of the body with a given element material, the more elements should be used to give the necessary stability of the body.

The flexible tubular body according to the present invention has been found to be quite suited for use as a prosthesis for transluminal implantation in blood vessels or other similar organs of the living body. The tubular body is inserted into place in the organism in contracted state, i.e. with reduced diameter. After the tubular body according to the invention has been inserted into position it is subjected to expansion and can stay in place in expanded state by self-fixation if the diameter of the body in unloaded condition is selected somewhat larger than the diameter of the surrounding wall. This results in a certain permanent pressure of engagement against the inner wall so as to ensure good fixation.

This implantation process is quite simpler and less risky than the known implantation technique involving a non-expansible prosthesis. The radially contracted prosthesis which e.g. is inserted through the wall of the vessel at a distance from the implantation site will be fixed without the need for conventional removal of the parts of the organ to be replaced. In this manner the blood flow can be maintained even during the implantation which calls for a short period of time. The prosthesis need not be stitched to the vessel and already after a few days it has been definitely fixed to the body by means of natural tissue growth and after a few months the tissue growth is complete and the inside wall of the prosthesis is covered by new natural tissue.

The flexible tubular body can be brought to expand radially in several ways. It has been found for many reasons that it is preferred that the body has the property entering into radially expanded and unloaded position by itself. The expanded state of the body may be dependent on the inherent rigidity of the thread elements, but it may also be controlled by elastic strings, bands or membranes which are arranged in connection to the mantle surface of the body and extend axially along same. By their elasticity these strings, bands or membranes result in axial traction of the body, i.e. to bring same to take an expanded state.

An alternative way of imparting properties to the body through which it tends to take a radially expanded position is to attach the elements to each other at the points of crossing thereof in a suitable manner, for example by some form of welding, gluing or the like.

The elements forming the flexible tubular body should be made of a medicinally acceptable material, for example plastic or metal, and they should possess certain springiness or rigidity combined with suitable elasticity. The elements may be built up as monofilaments, for example polypropylene, dacron or other suitable plastic or constituted by a composite material. They may also be made from some suitable medicinally acceptable metal, for example steel.

The free ends of the thread elements of the tubular body can be modified or protected in several ways. The alternative in which no free ends at all are present is the alternative to make the tubular body as a whole of one coherent element. The alternative which is most closely related to that is the case where the free ends of a body resulting from severing a long string are connected with U-shaped members which are attached to the ends of the elements pair-wise in a suitable manner, for example heat welding, gluing or the like. In this manner elements of the same direction of winding or elements of the opposite direction of winding can be attached to each other two and two.

An alternative to these embodiments is to weld together the points of crossing in a ring around the material by electric resistance heating or the like before severing the string, severing then taking place adjacent to and just outside the welding site. The ends then extending outside the welding area may be folded inwardly towards the interior of the body with light plastic deformation, for example through controlled heating. Yet another alternative consists in bending the free ends of the elements to form loops.

As previously indicated the tubular body according to the present invention is suited for use as so-called graft. In this case the body may function as a graft namely if it is made of elements of such character as to impart by themselves the desired density and porosity to the body to function as a graft whereby at least a number of the elements may be made of polyfilament materials or the like. The alternative of the elements themselves imparting the desired density to the body is to apply some sort of surface layer to the body, for example of plastic or other suitable material. By applying such surface layer the crossing points may at the same time be fixed as indicated above so as to make the body tend to take an expanded position.

Outside or inside or amalgamated with the body there may also be arranged a separate sleeve or membrane. This can be constituted by a stocking of porous web surrounding the body which can be implanted together with the body. In this case the stocking may either by stretchability in the web or by overlapping folding or in another manner, for example by being built up in accordance with the same principle as the body from a plurality of thread elements, be adjustable to the body in connection with the expansion thereof. It is also possible to conceive the use of some form of tricot type product or crimped fibre textile. When using such a separate member it is preferred that it is axially fixed relative to the body so as to end up in the right position when applied in a large vessel or the like.

The expansion or contraction of the tubular body can be provided by a device with means which are arranged to elongate or shorten the body. Such means may be designed in many ways, for example so that their construction allows axial movement of the ends of the body relative to each other to reduce or increase the diameter of the body. The device should include gripping members capable of gripping the ends of the body and axially moving same relative to each other. The gripping members should be arranged so as to be releasable after the application of the body at the desired site so that the device except for the body can be removed from said site. Alternatively, the device may include a flexible tube within which the tubular body is intended to be placed in contracted state, and operating members by means of which the body under expansion thereof can be pushed out of the tube to be applied at the desired site.

Other characterizing features are obvious from the appended patent claims.

EXAMPLES

The invention will in the following be described by non-limiting but exemplifying embodiments in connection to the appended drawing. In the drawing these embodiments are illustrated and.

Figure 1A:
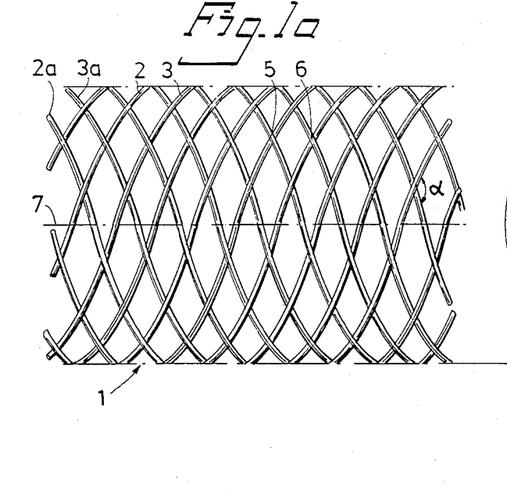
FIG. 1A and FIG. 1B show diagrammatically a side view and an end view, respectively, of the flexible tubular body according to the invention.
Figure 1B:
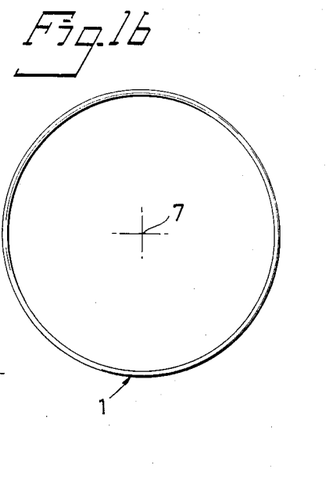

In FIGS. 1a and 1B there is shown an example of a prosthesis in the form of a cylindrical tubular body generally designated 1. As is clear from FIG. 1A the mantle surface of body 1 is formed by a number of individual thread elements 2, 3 etc. and 2a, 3a etc. Of these elements elements 2, 3 etc. extend in helix configuration axially displaced in relation to each other having the center line 7 of body 1 as a common axis. The other elements 2a, 3a extend in helix configuration in the opposite direction, the elements extending in the two directions crossing each other in the manner indicated in FIG. 1A.

Figures 2A, 2B, 3:
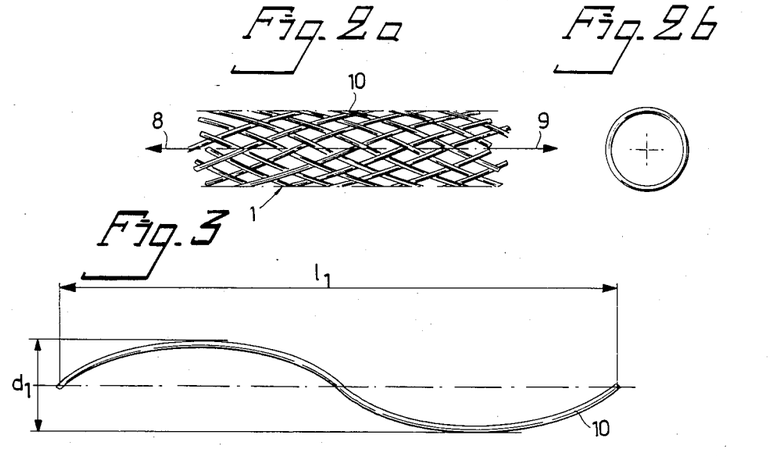
FIG. 2A and FIG. 2B show the same tubular body as in FIG. 1 but in contracted state.
FIG. 3 and FIG. 4 show one separate thread member of the body, the body being shown in contracted and expanded state, respectively.

The diameter of a tubular body built up in this manner can be varied if the ends of the body are axially displaced relative to each other in the direction of the center line 7. In FIG. 2A there is illustrated how the tubular body 1 according to FIG. 1A has been given reduced diameter by moving the ends 8, 9 away from each other in the direction of the arrows. FIG. 1B shows the diameter of the tubular body in an expanded state, whereas FIG. 2B shows the diameter of body 1 in contracted state after the ends 8, 9 thereof have been moved away from each other.

Figure 4:
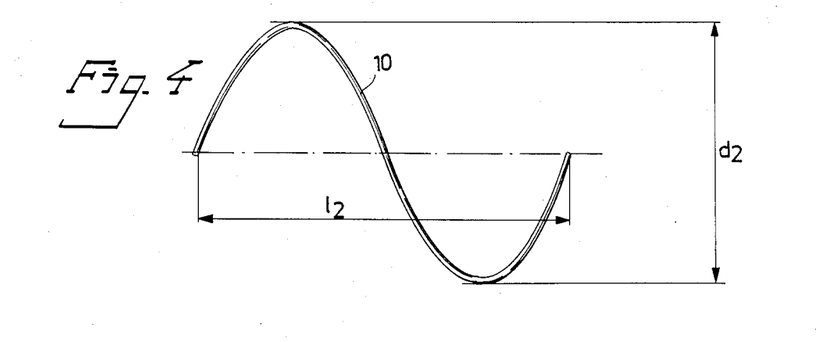

FIGS. 3 and 4 show a detail picked from FIGS. 1 and 2, more particularly one single thread element of the tubular body 1 and how its helix configuration will be changed in connection with the change of the length of the tubular body 1.

In FIG. 3 the individual element 10 corresponding to element 10 of FIG. 2A is shown. The diameter of the helix is $d_1$ and the length of the element is $l_1$. In FIG. 4 the same element 10 is shown after the tubular body has been expanded to the state shown in FIG. 1A. The diameter of the helix has now increased and is designated $d_2$, whereas the length has decreased and is designated $l_2$.

Figure 7:
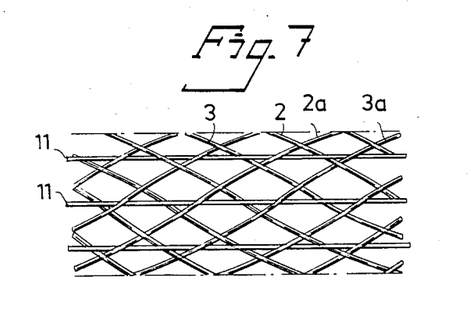
FIG. 7 shows an alternative embodiment of the tubular body.

The tubular body 1 can be expanded in a number of ways. As previously mentioned it is preferred that the body inherently has the property of taking expanded position by itself in unloaded condition. In the present disclosure the expression "expanded position" always refers to radial expansion, i.e. a state with a large diameter of body 1. The self-expanding property can be obtained by providing the body with strings or bands extending parallel and axially with the mantle surface of the body. An example of such embodiment is shown in FIG. 7 where the tubular body 1 is provided with axial strings or bands 11. These strings or bands 11 are suitably made of an elastic material and they are fixed to the elements of the tubular body 1 in a suitable manner and with the body in expanded state. Now, if the tubular body 1 is axially elongated by removing the two ends thereof from each other the elastic strings or bands 11 will be stretched. After removal of the tensile force from the body 1 the elastic strings or bands 11 will compress the body 1 in an axial direction resulting in a corresponding increase of the diameter of the body.

The tubular body 1 can be provided with the same tendency to take expanded position by fixing the elements 2, 3 etc.; 2a, 3a etc. at the crossing points 5, 6 (FIG. 1), as previously mentioned. Another way of providing this effect is to provide for an interior or exterior tubular elastic member, for example of a thin elastomer, which is attached to at least both ends of the tubular body.

Figure 5:
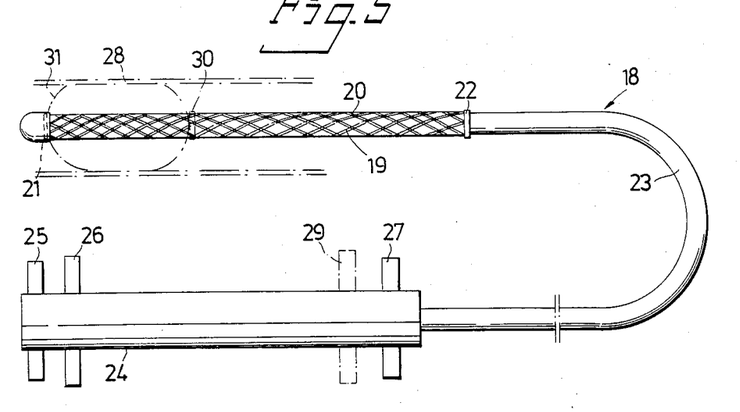
FIG. 5 shows diagrammatically an assembly incorporating the tubular body according to the present invention.

In FIG. 5 there is shown a device generally designated 18 to enable insertion of the tubular body 20 in contracted and elongated state at the desired site of for example a blood vessel. The tubular body 20 surrounds the forward tubular part 19 of apparatus 18 and is attached at both ends thereof to gripping means 21 and 22. The forward tubular part 19 of the apparatus is connected to an operational member 24 through a flexible tubular means 23. By means of operational elements 25, 26 and 27 of the operational member 24 the gripping means 21 and 22 can be controlled in a desired manner.

In FIG. 5 there is shown diagrammatically how apparatus 18 with the contracted tubular body 20 has been inserted into for example a blood vessel which in the figure is shown with dashed lines and designated 28. Operational member 24 is connected with gripping member 22 in such a manner that when the operational means 26 is moved forwardly to position 29 shown with dot and dash lines a gripping member 22 is displaced in a corresponding manner to the dot and dash line position 30. As a result the end of tubular body 20 has been moved from position 22 to position 30, whereas in this case the other end of the body remains in position 21. At the same time the diameter of body 20 has increased and when the end has reached position 30 the body 20 is expanded, i.e. it has been brought into contact with the interior wall of the vessel and has taken dash-dotted line position 31. Since both ends of the tubular body 20 still are held by members 21, 22 body 29 in expanded state takes a balloon-like shape.

Operational means 27 is also connected with the gripping member 22 by means of a part, for example a wire, running in tubular member 23. In this manner gripping member 22 in its position 30 can be manoeuvred by axial displacement of operational member 27 to release the end of the body 20. In the same manner manoeuvring means 25 which is connected to gripping member 21 can release the forward end of the tubular body from gripping member 21 by axial displacement thereof. The ends of the elastic body 20 are thereby immediately subjected to movements relative to each other to provide for expansion and the prosthesis takes its expanded cylindrical shape in the interior of the blood vessel.

Figure 6:
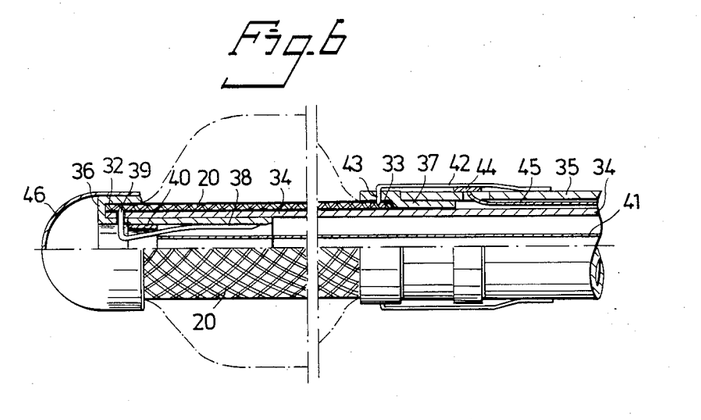
FIG. 6 shows in an enlarged view part of the assembly of FIG. 5.

In FIG. 6 there is shown more in detail and in enlargement the construction of the forward tubular part 19 of device 18. The tubular body 20 with its both ends 32 and 33 surround a thin-walled flexible tube 34 running inside and concentrically to an outer flexible tube 35, the two tubes of which form the tubular member 23 in FIG. 5. At the front part of the inner tube 34 an annular member 36 is arranged, into which the end 32 of tube 20 is inserted. In a corresponding manner the end 33 of tube 20 is inserted into an annular member 37 which is axially displaceable in relation to the tube 34 surrounded by ring 37. At the front part of tube 34 there is provided an interior gripping member or latch 38. Latch 38 which is suitably made of spring steel, has a forward pointed part 39 bent under about right angle. This part 39 extends radially outwardly through a hole in tube wall 34. It can move in radial direction under the influence of a ring 40 which is axially movable and arranged inside tube 34. Ring 30 is connected to a wire 41 through which by axial displacement latch 38 can be moved in a radial direction. In FIG. 6 latch 38 is shown in such position that its pointed part 39 has perforated the end 32 of body 20 and thus maintains said end in position.

In the corresponding manner another latch 42 is arranged to hold from the outside the end 33 of the tubular body 20 by its pointed part 43. This latch 42 which is attached to the outside of tube 35 can be moved in radial direction by means of a ring 44 arranged about tube 35 and attached to a cable 45 extending between tubes 34 and 35. Cables 44 and 45 are connected to the operational means 25 and 27, respectively, in FIG. 5.

When the attached and axially extended tubular body 20 shall be released from the remaining part of the device after the axial expansion of the body this takes place by releasing the pointed parts 39, 43 of latches 38 and 42, respectively, from the ends of tubular body 20 by actuating rings 40 and 44 through operational members 25 and 27 via cables 41 and 45 so as to deflect latches 38 and 42. Ends 32 and 33 of body 20 will then be released by axial displacement of the tubular part 19 of the apparatus. As is clear from FIG. 6 the front end of the apparatus is protected by a hub or casing 46 attached to ring 36.

Figure 8:
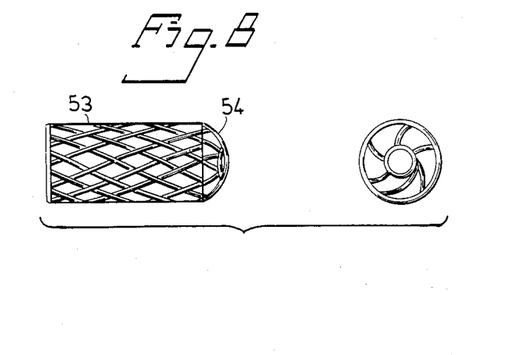
FIG. 8 shows the tubular body designed as a combined graft and filter.

As previously indicated the expansible tubular body finds several applications within surgery. For example, in the embodiment shown in FIG. 1 it can be utilized for supporting vascular walls. In FIG. 8 there is shown a modified embodiment of the flexible tubular body. In this embodiment the body consists of a cylindrical circular part 53 which at one end thereof changes to a diminishing part or end 54 also built up from thread elements. This device has been found to be suitable for use as a sieve or filter to prevent thrombosis. The device shown in FIG. 8 can be applied at the desired location within a blood vessel, for example Vena Cava Inferior, for the purpose of preventing lung emboly. Previously known filter means intended for application within blood vessels for the purpose of catching thrombosis are associated with the disadvantage that they are permanently attached in the blood vessel by pointed ends or latches or the like, positional correction or removal of the filter not being possible. An example of such device is described in U.S. Pat. No. 3,540,413. The device according to the present invention can be inserted into Vena Cava with great precision and it does not involve any risk for damages on surrounding vascular walls which is the case with known devices used today in surgery for the same purposes.

Figure 9:
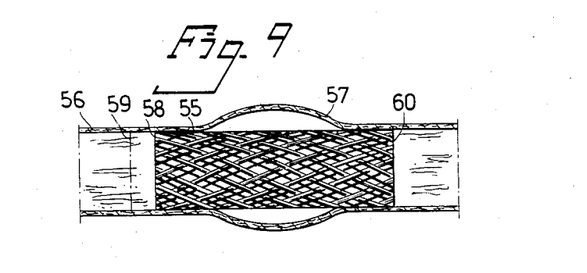
FIG. 9 shows the tubular body used as a graft in connection to aneurism.

In FIG. 9 there is shown a tubular body according to the present invention for use as a graft. In this case body 55 has a much denser wall than the embodiment shown in FIGS. 1 and 2. This denser wall can be obtained by weaving an elastic yarn between the supporting thread elements 2, 3 etc.; 2a, 3a etc. of FIG. 1. In this manner a wall having a controlled porosity can be obtained. This tubular body having a more or less porous wall is thus a sort of expansible graft and has versatile use.

In the application shown in FIG. 9 body 55 is implanted into an aorta 56 wherein there is an aneurism 57 in the form of a widening of the vascular wall. In view of the fact that the expansible body or graft 55 can be inserted at a distance from the damaged location of aorta and then located in the middle of the aneurism the latter will be bridged and need not be operatively removed. In FIG. 9 it is also indicated that aorta is a conical blood vessel. Therefore, the procedure in this case will be that the prosthesis in the form of a graft is inserted with an instrument, for example in accordance with FIG. 5. After being located the graft or body 55 is expanded. In view of the conical configuration of aorta the surgical techniques will be as follows.

The front end 31 of graft 55 according to FIG. 5 is inserted somewhat further into aorta than the location it shall take after terminated operation. This position 59 is indicated in FIG. 9 with dash-dotted line. The other end 22 of the axially extended graft 55 according to FIG. 5 is carried up to the final position corresponding to position 60 of FIG. 9 before the radial expansion. Since this part of aorta has a somewhat smaller diameter than the diameter in front of the aneurism as seen upstream in relation thereto the prosthesis cannot expand more than the dimension corresponding to the diameter at end 60. This is, however, alleviated by then moving the other end of graft 55 by means of the front part of the instrument from position 59 to position 58 so that this end of the graft can expand sufficiently to engage this part of the vascular wall.

Figure 11:
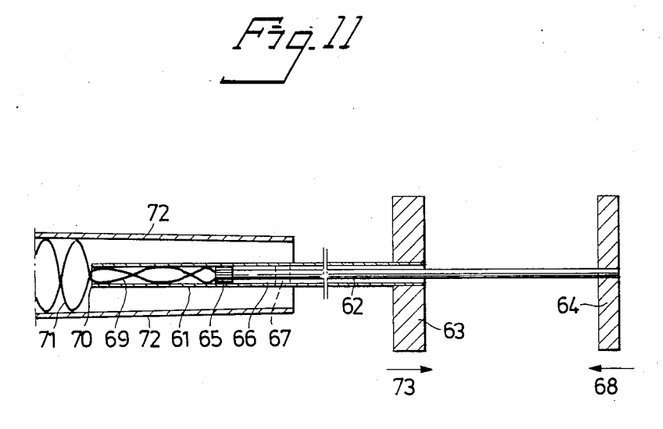
FIG. 11 shows diagrammatically an alternative assembly for manipulating the prosthesis of the invention.

In FIG. 11 there is shown another embodiment of the assembly for use in expanding the tubular body.

This assembly constitutes a flexible instrument intended to introduce the tubular body in contracted state into for example a blood vessel and then to expand the body when located therein. The parts of the instrument consist of an outer flexible tube 61 and a concentric also flexible inner tube 62. At one end of the outer tube an operational member 63 is arranged. Another operational member 64 is attached to the free end of inner tube 62. In this manner the inner tube 62 is axially displaceable in relation to the outer tube 61. At the other end of inner tube 62 a piston 65 is attached which when moving runs along the inner wall of outer tube 61.

When the instrument is to be used the tubular expansible body 69 in contracted state is first placed inside tube 61, the inner tube 62 with the piston 65 being located in the rear part 66 of outer tube 61. The starting position of piston 65 is shown by dashed lines at 67 in FIG. 11. In this manner part of tube 61 is filled with the contracted tubular body 69 in the starting position.

During implantation the flexible tubular part of the device is inserted to the location of a blood vessel intended for implantation. Member 64 is then moved in the direction of arrow 68, the contracted body 69 being pushed out through end 70 of tube 61, the part of the tubular body 69 leaving tube end 70 expanding until in its expanded position 71 it is brought to engagement with the interior of vascular wall 72. The tubular body 69, 71 is for sake of simplicity shown in FIG. 11 as two sinus-shaped lines. To the extent that the expanded body 21 comes into engagement with vascular wall 72 tube end 70 is moved by moving member 63 in the direction of arrow 73. The contracted body 69 is moved by the piston 65 pushing against one end of the body. Thus, the implantation takes place by simultaneous oppositely directed movements of members 64 and 63, the displacement of member 64 being larger than that of member 63. When the contracted body 69 has been fully removed from the tube 61 the expansion is terminated and the instrument can be removed from the location of the operation.

The embodiment according to FIG. 11 has the great advantage that the constructional details are quite simple and can be operated with high reliability. The instrument shown is also suitable for implantation of helices with very small diameters. As an example there may be mentioned that experiments have been performed with a tubular expansible body consisting of crossing thread elements, the contracted diameter of the body being only 2 mms and the expanded diameter 6 mms. It is also fully conceivable to implant expanded bodies with even smaller diameter. The instrument according to FIG. 11 may also advantageously be used for implantation of bodies in the form of grafts of a very large diameter.

In implantation of long bodies it is conceivable that the resistance in displacing same in tube 61 becomes too high. In this case it may be suitable to replace piston 65 at the front end of tube 62 with movable jaws or latches which operate in such a manner that when tube 62 is brought forward in the direction of arrow 68 the latches engage the inner side of body 69, the body being brought forward. When tube 62 is brought back in the direction of arrow 73 the latches are released. In this manner body 69 can be moved forwardly by a pump-like motion of tube 62.

Many embodiments of the different members shown in FIG. 11 are, of course, conceivable. Thus, it is possible for example to simplify implantation for the surgeon by controlling the relative motion between members 63 and 64 in a mechanical manner.

It is essential that the expansible body possesses certain elastic properties in order to enable successful implantation. For example, when the body is inserted to keep blood vessels open or is implanted as blood vessel prosthesis it should have elastic properties which are as similar as possible to those of the blood vessel of the living body. The body must also remain fixed against the surrounding organ, for example the blood vessel, during the stress and strain the organ is subjected to. The body must at the same time be elastically resilient radially and axially so as to have for example sufficient adaptability to follow pulsation of the blood or the bending of a limb. The body shall also have sufficient inherent rigidity so as to maintain its shape at for example external pressure and must have sufficient strength to resist internal pressures.

In order to obtain these properties it is suitable carefully to select and adapt materials and dimensions on the thread elements of the body to the actual area of application. In addition to the obvious requirement that the material of the thread elements shall be compatible with the tissue, i.e. inter alia result in minimum reaction of rejection, the non-toxic and enable cell growth, it may be generally said that the material should be rigid and elastic and not plastically deformable to any significant extent. The material may for example be monofilaments of polyesters, polyurethanes, polycarbonates, polysulphides, polypropylene, polyethylene, polysulphonates, stainless steel, silver. The diameter of the monofilament should suitably lie within the range 0.01 to 0.5 mms.

It has been found that in certain cases it is important that the angle $\alpha$ between the thread elements of the body, for example between 2 and 2a of FIG. 1A, when the body is expanded or is in an unloaded or nearly unloaded state is sufficiently large, inter alia to meet the above requirements. It has been found that the greater the angle $\alpha$ the higher the stability of the body under external pressure. The ideal from this point of view would be 180°, which is not practically possible. The angle as shown in FIG. 1A is about 160°, which normally is close to the upper limit.

Figure 10:
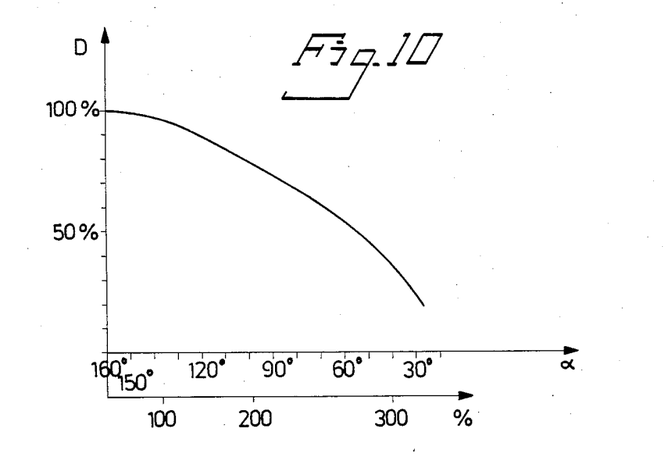
FIG. 10 shows a diagram of the diameter (D) of the body as a function of the angle $\alpha$ and of the elongation of the prosthesis in %.

In order to change the diameter of the body it is required, as indicated, that both ends of the body are axially displaced relative each other. In FIG. 10 there is shown the general relation between this movement. The change in percent in diameter when the ends are moved away from each other has been plotted along the y-axis and along the x-axis the corresponding change in percent in length expressed as elongation. Along the x-axis there has also been plotted the angle $\alpha$ as a function of the diameter of the body.

As is shown from FIG. 10 the relative diameter reduction is small at the outset of the elongation process and the diameter has been reduced to the order of 90% when the elongation is 100% referring to the starting position where the angle $\alpha$ is as close to 180° as is practically possible. At an elongation of 200% the diameter reduction is 75% corresponding to an angle $\alpha$ of 100°.

The diameter reduction will then be accelerated at increasing elongation. Thus, an elongation increase from 250 to 300% results in a diameter reduction from 60% to 30%, i.e. a relatively large diameter change at a relatively small elongation. Within this range the angle is reduced from about 70° to 40°. As indicated above it is in some cases desirable that the expanded body takes a position which is as far to the left on the curve of FIG. 10 as possible, i.e. the angle $\alpha$ should be as large as possible. Since the implanted body must engage against the vascular wall with certain pressure in order to remain fixed the diameter of implantation must be smaller than the diameter at free expansion.

When using expansible bodies according to the invention for implantation in blood vessels or other tubular organs the necessary expansion forces may be provided for example by elastic means, such as longitudinally extending elastic strings fixed at the crossing thread elements of helix configuration. By selecting a large angle $\alpha$ when the elastic means are fixed to the elements the requirements previously mentioned may be met in a simple manner.

The reason why a large value of the angle $\alpha$ is often desirable is the fact that the elastic properties of the prosthesis are impaired with decreasing angle. Under for example exterior pressure in a radial direction the resistance to deformation is small and there is a risk for local axial displacement between prosthesis and vascular wall, which can prevent cell growth at the site of displacement. Another reason for selecting a high value of the angle $\alpha$ is in those cases where a high expansion ratio is desired, i.e. a high ratio between diameter of the expanded body and the diameter thereof in contracted state. In order to obtain for example expansion ratio over 2 up to about 3 the angle $\alpha$ should exceed about 120°. The selection of the angle $\alpha$ is also depending on the material of the thread elements of the prosthesis. If a plastic material has been selected too small an angle $\alpha$ results in too high resiliency in radial direction. In some other cases it may, however, be desirable to select a smaller angle $\alpha$, namely in those cases where pronounced radial yield is desired.

Another case where a high value of the angle $\alpha$ might be desirable is applications wherein the prosthesis as applied will be subjected to a bending. The resistance to flattening of the prosthesis will thus be higher the larger the angle $\alpha$. Thus, it is suitable to select an angle $\alpha$ which is more than about 60°, and an obtuse angle $\alpha$ could be particularly suitable. To provide for high resistance to external pressure or to enable high expansion ratios it is preferred to select an angle $\alpha$ of at least about 120°.

From FIG. 10 it is clear that the body must be highly extended when using large angles $\alpha$. To enable transluminal implantation through passages of small diameters the elongation starting from large angles $\alpha$ may be substantial and can be up to 300% and even more.

When implanting for example vessel prostheses or similar devices, for example to keep blood vessels open, it is as a rule desirable to reach a pressure against the surrounding vascular wall which is at least about 100 mm Hg. There is also a highest pressure which must not be exceeded. This highest pressure varies from case to case but should not exceed about 500 to 1000 mm Hg when used as a vascular prosthesis. If the desired pressure will be provided by longitudinally extending elastic members or an elastic sleeve or membrane the necessary pressure for fixation can be obtained with reasonable forces when selecting a large angle α which is advantageous. Thus, calculations show that in smooth cylindric engagement between vascular prosthesis and surrounding vascular wall there is required a total force of a few Newtons (~0.1-0.2 kp) to obtain fixation if the angle α is 150°-170°. This fact also contributes to reduced risk of displacement of the implanted prosthesis under external pressure since the frictional forces arising are sufficient to prevent such displacement. If the angle α is for example 45° there is, however, required a force of about 10-20 Newtons (1-2 kp) which is practically disadvantageous.

In order that the prosthesis of the invention shall operate in a satisfactory manner, inter alia to give the necessary fixation when applied, such requirements must be met in regard to the elastic material resulting in the necessary expansive force. The material must also result in acceptable adherence to the thread elements of the body and must, of course, be biologically acceptable for implantation. The material shall thus have a low module of elasticity and should present a linear relation between force and elongation at least up to 250-600% elongation and must not possess significant hysteresis.

There are a group elastomers meeting the above requirements which have been found suitable for use in manufacturing expansible bodies according to the invention. Such elastomers are included within the group of materials called segmented polyurethanes (PUR), several of which are commercially available under trade names such as Pelethane (UpJohn), Biomer (Ethicon), Estane Goodrich. These materials can be dissolved in suitable solvents to form solutions, from which thin elastic bands or thin-walled tubes can be prepared for attachment to the supporting thread elements of helix configuration forming the framework of the body.

When using prosthesis according to the invention as so-called grafts or vascular prostheses the wall of the prosthesis, as previously mentioned, should be porous, thin and compatible with tissue and be composed so as to enable growth of natural tissue, inter alia neointima. Segmented polyurethanes (PUR) are also suited for use to form such walls since the said properties can be combined with the requirement of a wall having a very high elasticity. Such walls may be prepared in the form of a thin tube consisting of fibres of segmented PUR formed by extrusion from a solution of PUR. The fibres are attached to each other at the crossing points and the wall can be made with the desired porosity by suitable adjustment of for example fibre thickness and density. The resulting tube can surround the body or can be attached to the inside thereof. Alternatively, the thread elements of the body can be amalgamated with the tube material, suitably when preparing the tube.

In order to impart the desired expansional force to a vascular prosthesis bands of PUR may be combined with suitable porous wall material which can consist of monofilaments or multifilaments interwoven between the thread elements of the body or which can consist of a porous elastic wall prepared according to what has been described above.

In certain cases it may be suitable to make the body or its bonds, sleeve or membrane from a biologically degradable material, for example polylactide and/or polyurethane.

Below there are given non-limiting examples of embodiments wherein the inventive principle has been applied.

EXAMPLE 1

Vascular graft

Expanded diameter 20 mms
Angle α 160°
Length 100 mms
Suited for implantation in aorta within the diameter range 15 mms-18 mms
Smallest diameter before implantation 8 mms
Total elongation about 300%
Calculated axial force for fixation 0.1 kp provided by a microporous elastic PUR-wall having a thickness of 0.15 mms
Pore size 15-50 μm
Thread element material: polyester monofilament having a diameter of 0.15 mms
Number of elements n=72 (2×36)

EXAMPLE 2

Vascular prosthesis against stenosis

Expanded diameter 6 mms
Angle α 100°
Length 200 mms
Implantation in veins within a diameter range 4-5 mms
Total elongation 250%
Axial force for expansion 0.08 kp provided by 4 elastic bands of segmented PUR, each having a width of 1.5 mms and a thickness of 0.3 mms
Thread element material: polypropylene monofilament having a diameter of 0.09 mms and number of elements n=36 (2×18).

Two or more tubular bodies can be concentrically arranged on top of each other to impart improved stability to the body. This is particularly useful when using thread elements having a small diameter and/or when the number of elements is small.

I claim:
1. An implantation device for complete insertion and implantation of a prosthesis in a body vessel comprising in combination:
   (a) the prosthesis having a radially and axially flexible, elastic tubular body with a predetermined diameter that is variable under axial movement of ends of the body relative to each other and which is composed of a plurality of individually rigid but flexible and elastic thread elements each of which extends in helix configuration along the center line of the body as a common axis, the flexible and elastic elements defining radially self-expanding body, said body provided by a first number of elements having a common direction of winding but be axially displaced relative to each other and crossing a second number of elements also axially displaced relative to each other but having an opposite direction of winding, the crossing of the first and second elements defining at least an obtuse angle; and
   (b) load applying means placing said tubular body in a reduced diameter state prior to the insertion, said load applying means removed from said body after said insertion of the tubular body so as to permit said tubular body to radially self-expand in the vessel.

2. A prosthesis according to claim 1, wherein the crossing elements are arranged in a braidlike configuration so as to impart stability to the body.

3. A prosthesis according to claim 1, wherein the number of elements in the body is N, where N is at least about 10.

4. A prosthesis according to claim 3, characterized thereby that the number of elements in each direction of winding is n/2.

5. A prosthesis according to claim 1, wherein the body is arranged to take a radially expanded postion by means of elastic members, which members extend axially along the mantle surface of the body and exert bias to axially compress the body.

6. A prosthesis according to claim 1 characterized thereby that the body inherently tends to take radially expanded position due to the fact that the thread elements are attached to each other at the crossing points.

7. A prosthesis according to claim 1, characterized by a membrane of a porous material coextensive with the body along the major part of its length.

8. A prosthesis according to claim 1, characterized thereby that the body at at least one end thereof is designed with diminishing diameter so as to act as a filter when applied.

9. A prosthesis according to claim 5, characterized thereby that said members or membrane are made of a preferably porous material comprising segmented polyurethane.

10. A prosthesis according to claim 2, wherein the number of elements in the body is N where N is at least about 10.

11. A prosthesis according to claim 7, characterized thereby that said members or membrane are made of a preferably porous material comprising segmented polyurethane.

12. A device according to claim 1, wherein an axially directed angle ($\alpha$) between crossing elements is at least 120°.

* * * * *

REEXAMINATION CERTIFICATE (2988th)

United States Patent [19]

Wallsten

[11] B1 4,655,771

[45] Certificate Issued Sep. 10, 1996

[54] PROSTHESIS COMPRISING AN EXPANSIBLE OR CONTRACTILE TUBULAR BODY

[75] Inventor: Hans I. Wallsten, Denens, Switzerland

[73] Assignee: AMS Medinvent S.A., Crissier, Switzerland

Reexamination Request:
No. 90/003,752, Mar. 20, 1995

Reexamination Certificate for:
Patent No.: 4,655,771
Issued: Apr. 7, 1987
Appl. No.: 571,549
Filed: Apr. 11, 1983

[22] PCT Filed: Apr. 11, 1983
[86] PCT No.: PCT/SE83/00131
   § 371 Date: Dec. 7, 1983
   § 102(e) Date: Dec. 7, 1983
[87] PCT Pub. No.: WO83/03752
   PCT Pub. Date: Nov. 10, 1983

[51] Int. Cl.⁶ .......................................... A61F 2/06
[52] U.S. Cl. .................... 623/1; 623/12; 623/66
[58] Field of Search .................. 623/1, 11, 12, 623/66

[56] References Cited

U.S. PATENT DOCUMENTS

| | | | |
|---|---|---|---|
| 2,836,181 | 5/1958 | Japp | 128/334 |
| 2,936,257 | 5/1960 | Nailler et al. | 154/2.22 |
| 3,105,492 | 10/1963 | Jeckel | 128/334 |
| 3,215,768 | 11/1965 | Murphy | 174/36 |
| 3,463,197 | 8/1969 | Slade | 138/125 |
| 3,657,744 | 5/1972 | Ersek | 3/1 |
| 3,730,835 | 5/1973 | Leeper et al. | 195/1.7 |
| 3,822,238 | 7/1974 | Blair | |
| 3,858,618 | 1/1975 | Kaufman | 138/149 |
| 3,952,747 | 4/1976 | Kimmell | 128/303 |
| 4,300,244 | 11/1981 | Bokrus | 3/1.4 |
| 4,441,215 | 4/1984 | Kaster | 3/1.4 |
| 4,474,630 | 10/1984 | Planck et al. | 156/62.4 |
| 4,503,569 | 3/1985 | Dotter | 128/343 |
| 4,553,545 | 11/1985 | Maass et al. | 128/341 |
| 4,610,688 | 9/1986 | Silvestrini et al. | 623/1 |
| 4,850,999 | 7/1989 | Planck | 623/1 |

FOREIGN PATENT DOCUMENTS

| | | |
|---|---|---|
| 1602513 | 1/1971 | France. |
| 2333487 | 7/1977 | France. |
| 2391709 | 12/1978 | France. |
| 2152142 | 5/1972 | Germany. |
| 2528273 | 8/1980 | Germany. |
| 2928612 | 1/1981 | Germany. |
| 1183497 | 3/1970 | United Kingdom. |
| 1205743 | 9/1970 | United Kingdom. |
| 1565828 | 4/1980 | United Kingdom. |
| WO80/01460 | 7/1980 | WIPO. |
| 80/02641 | 12/1980 | WIPO. |

OTHER PUBLICATIONS

Didcott, C. C., "Oesophageal Strictures: Treatment by Slow Continuous Dilatation", *Ann. Roy. Coll. Surg. Engl.*, vol. 53, pp. 112–127, 1973.

Dotter, C. T., "Transluminally–Placed Coilspring Endarterial Tube Grafts—Long-Term Patency In Canine Popliteal Artery", *Investigative Radiology*, vol. 4, pp. 329–332, Sep.–Oct. 1969.

*Primary Examiner*—David J. Isabella

[57] ABSTRACT

A prosthesis for transluminal implantation comprising a flexible tubular body which has a diameter that is variable by axial movement of the ends of the body relative to each other and which is composed of several individual rigid but flexible thread elements each of which extends in helix configuration with the center line of the body as a common axis, a number of elements having the same direction of winding but being axially displaced relative to each other crossing a number of elements also axially displaced relative to each other but having the opposite direction of winding; and method for transluminal implantation.

B1 4,655,771

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentablility of claims 1-12 is confirmed.

New claims 13-23 are added and determined to be patentable.

*13. A prosthesis according to claim 1 wherein the expanded prosthesis has a substantially uniform outer diameter.*

*14. A prosthesis according to claim 1 wherein the expanded prosthesis engages the vessel substantially along the entire axial length of the prosthesis.*

*15. A prosthesis according to claim 1 wherein the prosthesis includes an elastic member for providing radial force.*

*16. A prosthesis according to claim 1 wherein the prosthesis is covered with a surface layer.*

*17. A prosthesis according to claim 1 wherein the prosthesis includes a wall obtained by weaving elastic yarn between the elastic thread elements.*

*18. A prosthesis according to claim 17 wherein the wall has a controlled porosity.*

*19. A prosthesis according to claim 17 wherein the wall is made from segmented polyurethane.*

*20. A prosthesis according to claim 1 wherein the body contains a separate sleeve.*

*21. A prosthesis according to claim 20 wherein the sleeve is constituted by a stocking of porous web surrounding the body.*

*22. A prosthesis according to claim 20 wherein the sleeve is in the form of a tricot type product.*

*23. A prosthesis according to claim 20 wherein the sleeve is in the form of crimped fibre textile.*

\* \* \* \* \*